United States Patent
Larroque-Lahitette et al.

(10) Patent No.: US 9,345,518 B2
(45) Date of Patent: May 24, 2016

(54) BONE HOLDING DEVICE

(75) Inventors: Gilles Larroque-Lahitette, Lagor (FR); Richard Minfelde, Paris (FR)

(73) Assignee: Zimmer Spine (FR)

(*) Notice: Subject to any disclaimer, the term of this patent is extended or adjusted under 35 U.S.C. 154(b) by 326 days.

(21) Appl. No.: 13/504,230

(22) PCT Filed: Oct. 27, 2010

(86) PCT No.: PCT/EP2010/066223
§ 371 (c)(1),
(2), (4) Date: Jul. 23, 2012

(87) PCT Pub. No.: WO2011/051316
PCT Pub. Date: May 5, 2011

(65) Prior Publication Data
US 2012/0303065 A1    Nov. 29, 2012

(30) Foreign Application Priority Data
Oct. 27, 2009  (EP) .................................. 09306021

(51) Int. Cl.
*A61B 17/70* (2006.01)
*A61B 17/82* (2006.01)
*A61B 17/84* (2006.01)

(52) U.S. Cl.
CPC ......... *A61B 17/7002* (2013.01); *A61B 17/7053* (2013.01); *A61B 17/82* (2013.01); *A61B 17/842* (2013.01)

(58) Field of Classification Search
CPC .............. A61B 17/82; A61B 17/7022; A61B 17/7002; A61B 17/7053; A61B 17/842; A61B 17/7004; A61B 17/7062; A61B 17/707; A61B 17/864

USPC .......... 606/259, 277, 324, 74, 261, 263, 328, 606/278, 323
See application file for complete search history.

(56) References Cited

U.S. PATENT DOCUMENTS 2,049,361 A    7/1936    Johan
4,570,618 A    2/1986    Wu
(Continued)

FOREIGN PATENT DOCUMENTS

EP    1205152 B1    9/2004
EP    2052689 B1    12/2011
(Continued)

OTHER PUBLICATIONS

English language translation of WO 2007/036657 A1; accessed from epo.org on Jun. 12, 2015.*
(Continued)

*Primary Examiner* — Eduardo C Robert
*Assistant Examiner* — Julianna N Harvey
(74) *Attorney, Agent, or Firm* — Schwegman Lundberg & Woessner, P.A.

(57) ABSTRACT

A bone holding device comprising: at least one conformable elongated member (7) having a first portion (7a), a second portion (7b) and an intermediate portion (7c) therebetween; a rod (5) with at least one transverse passage (8) which opens into at least one of two opposite side faces of the rod, said passage (8) being delimited by inner surfaces (9) of the rod, and at least one compression member (14), the compression member and said inner surfaces (9) both defining clamping surfaces (14a, 9a) and cooperating so that the first and second portions (7a, 7b) of the elongated member (7) can be inserted and clamped between said clamping surfaces (14a, 9a). A method using such a device.

14 Claims, 5 Drawing Sheets

(56) References Cited

U.S. PATENT DOCUMENTS

| | | | |
|---|---|---|---|
| 5,030,220 A | 7/1991 | Howland | |
| 5,304,178 A | 4/1994 | Stahurski | |
| 5,356,412 A * | 10/1994 | Golds | A61B 17/1327 24/170 |
| 5,383,905 A * | 1/1995 | Golds | A61B 17/0487 24/136 L |
| 5,415,658 A * | 5/1995 | Kilpela | A61B 17/8861 606/297 |
| 5,772,663 A | 6/1998 | Whiteside et al. | |
| 5,810,825 A * | 9/1998 | Huebner | 606/74 |
| RE36,221 E | 6/1999 | Breard | |
| 5,935,133 A | 8/1999 | Wagner et al. | |
| 5,964,769 A * | 10/1999 | Wagner et al. | 606/74 |
| 6,053,921 A | 4/2000 | Wagner et al. | |
| 6,086,590 A | 7/2000 | Margulies et al. | |
| 6,179,838 B1 | 1/2001 | Fiz | |
| 6,277,120 B1 | 8/2001 | Lawson | |
| 6,299,613 B1 | 10/2001 | Ogilvie et al. | |
| 6,309,390 B1 | 10/2001 | Le Couedic et al. | |
| 6,391,030 B1 | 5/2002 | Wagner et al. | |
| 6,514,255 B1 | 2/2003 | Ferree | |
| 6,547,790 B2 | 4/2003 | Harkey, III et al. | |
| 6,605,091 B1 | 8/2003 | Iwanski | |
| 6,656,185 B2 * | 12/2003 | Gleason et al. | 606/74 |
| 6,682,533 B1 | 1/2004 | Dinsdale et al. | |
| 6,695,852 B2 | 2/2004 | Gleason | |
| 7,250,054 B2 * | 7/2007 | Allen et al. | 606/74 |
| 7,481,828 B2 | 1/2009 | Mazda et al. | |
| 7,959,654 B2 | 6/2011 | Mazda et al. | |
| 8,128,635 B2 | 3/2012 | Belliard et al. | |
| 2002/0116013 A1 | 8/2002 | Gleason et al. | |
| 2002/0177853 A1 * | 11/2002 | Chervitz | A61B 17/842 606/74 |
| 2009/0105715 A1 | 4/2009 | Belliard et al. | |
| 2009/0105717 A1 * | 4/2009 | Bluechel | A61B 17/8061 606/280 |
| 2009/0138048 A1 | 5/2009 | Baccelli et al. | |
| 2009/0177233 A1 | 7/2009 | Malek | |
| 2009/0182379 A1 | 7/2009 | Baccelli et al. | |
| 2009/0248077 A1 | 10/2009 | Johns | |
| 2009/0326585 A1 | 12/2009 | Baccelli et al. | |
| 2010/0249845 A1 | 9/2010 | Meunier et al. | |
| 2011/0034956 A1 | 2/2011 | Mazda et al. | |
| 2011/0112581 A1 | 5/2011 | Clement | |
| 2011/0238118 A1 | 9/2011 | Baccelli et al. | |
| 2011/0238125 A1 | 9/2011 | Baccelli et al. | |
| 2011/0301644 A1 | 12/2011 | Belliard | |
| 2012/0022591 A1 | 1/2012 | Baccelli et al. | |
| 2012/0022592 A1 | 1/2012 | Belliard | |
| 2012/0059377 A1 | 3/2012 | Belliard | |

FOREIGN PATENT DOCUMENTS

| | | | | |
|---|---|---|---|---|
| FR | WO 2007036657 A1 * | 4/2007 | | A61B 17/7053 |
| WO | 0154599 A1 | 8/2001 | | |
| WO | 0209604 A1 | 2/2002 | | |
| WO | WO 2007036657 A1 * | 4/2007 | | A61B 17/70 |
| WO | 2011012690 A1 | 2/2011 | | |

OTHER PUBLICATIONS

U.S. Appl. No. 13/384,180, filed Jan. 13, 2012 (30 pgs.).
U.S. Appl. No. 13/205,110, filed Aug. 8, 2011 (45 pgs.).

* cited by examiner

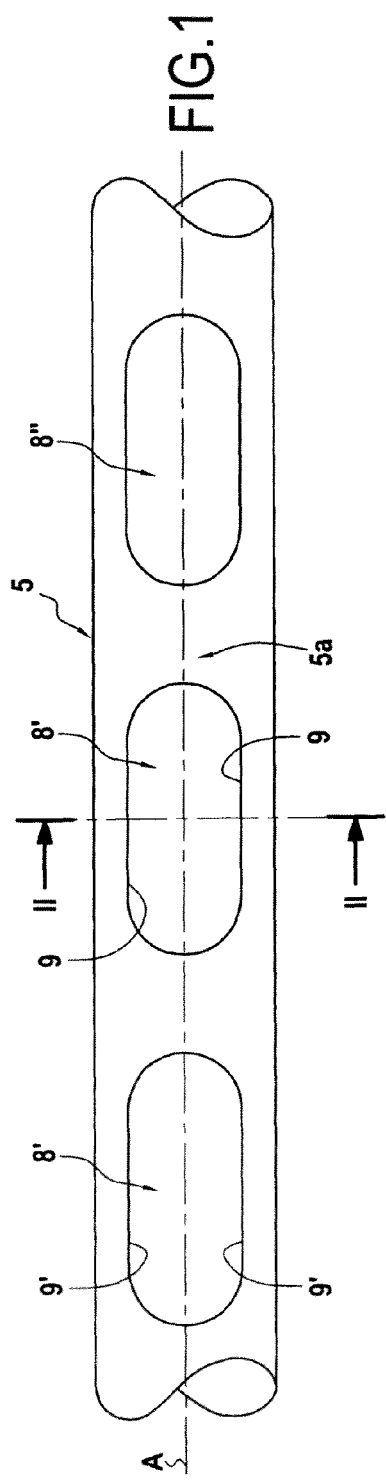
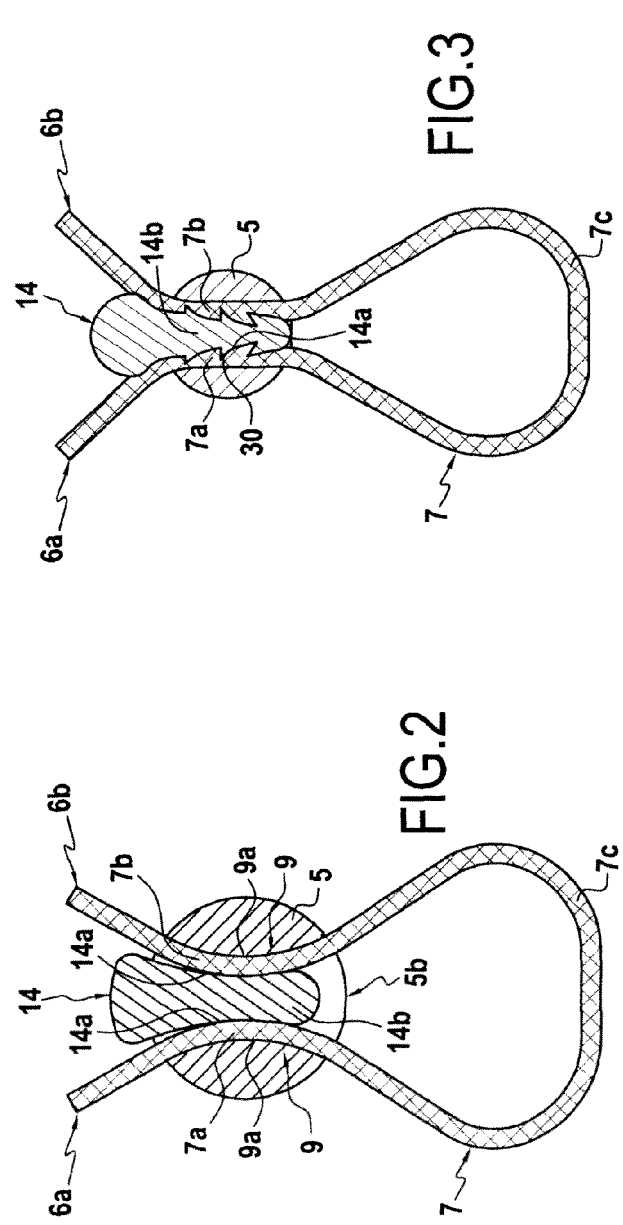

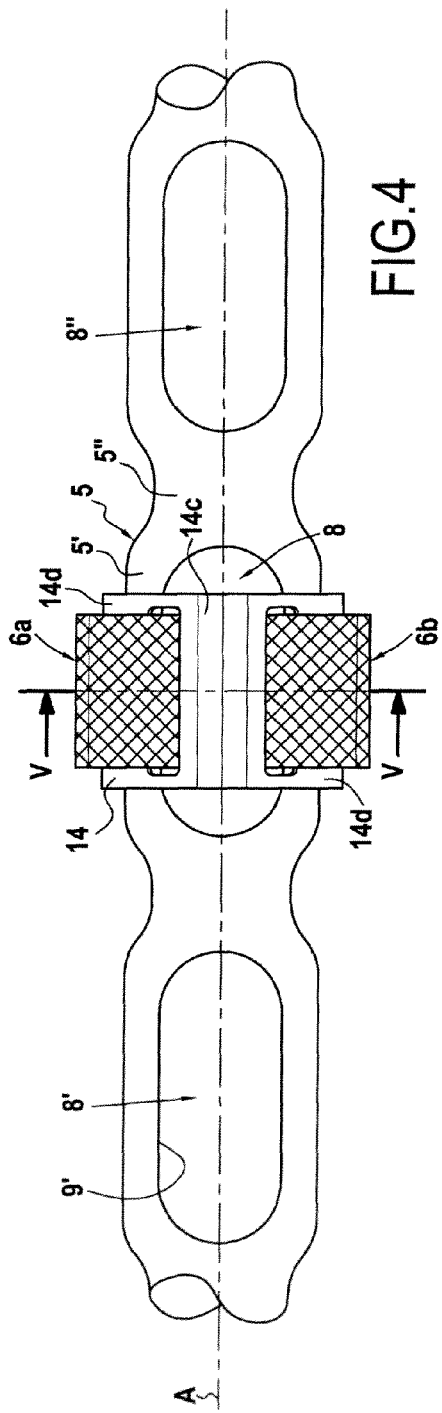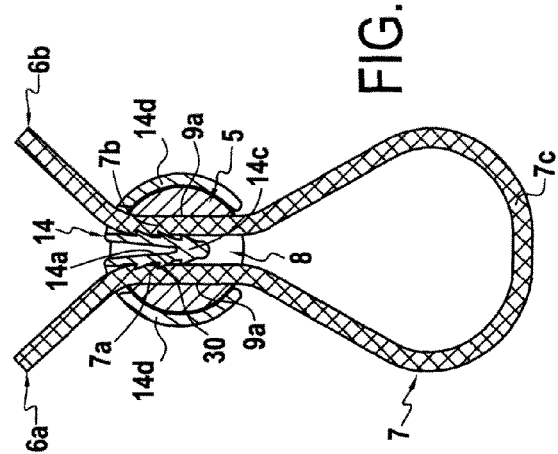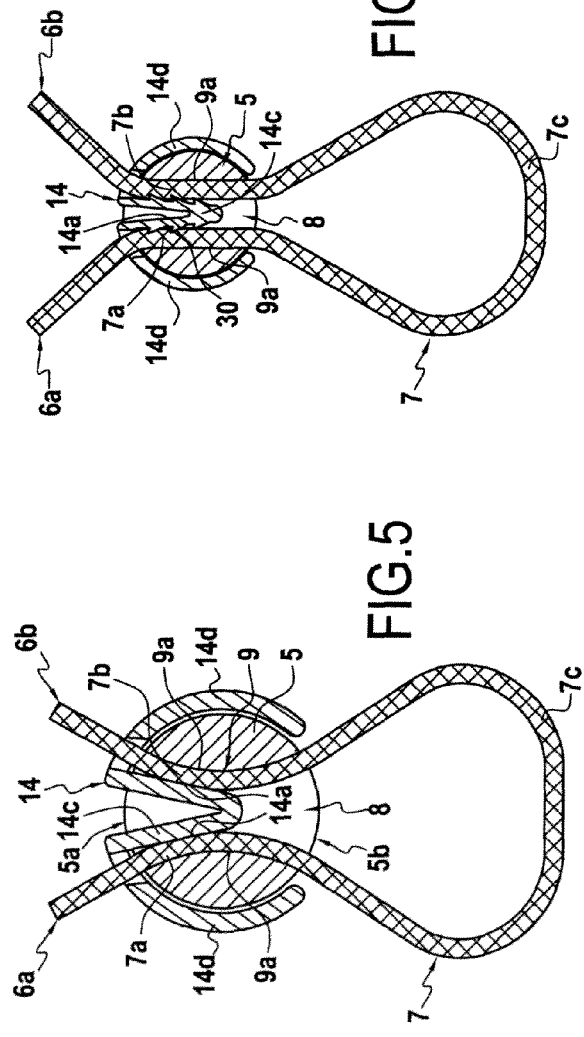

BONE HOLDING DEVICE

CROSS REFERENCE TO RELATED APPLICATIONS

This is a U.S. national stage application of International Application No. PCT/EP2010/066223, filed Oct. 27, 2010, entitled BONE HOLDING DEVICE, which claims priority from European Patent Application No. EP09306021.8, filed Oct. 27, 2009. All applications referenced herein are hereby incorporated by reference in their entireties.

FIELD OF THE INVENTION

The present disclosure relates to a device for holding a bone in a desired position and a method using such a device.

One possible application for the device is holding a bone in a desired position, for example, to aid in the healing of breaks, or holding several bony structures or bones, notably vertebrae, in relative positions, for example, to correct abnormal curvatures of the spine, which includes scoliosis treatment.

BACKGROUND OF THE INVENTION

The spine is formed of superposed vertebrae, from the lumbar vertebrae to the cervical vertebrae, each having an anterior part, which is the vertebral body, and a posterior part, which is the vertebral arch (or neural arch), the anterior and posterior parts enclosing the vertebral foramen. Each vertebral arch is formed by a pair of pedicles and a pair of laminae, and has transverse processes and/or a spinous process (or neural spine) projecting therefrom. The transverse and spinous processes project opposite to the vertebral foramen.

If the spine of a person has abnormal curvature, the vertebrae are abnormally inclined relative to one another. Typically, the lateral edges or the spinous processes of adjacent vertebrae are closer together or further apart than they should be.

As a remedy for this situation different kinds of known devices may be used to straighten the spine.

A first kind of device known in the art is a hook and rod device with hooks that are hooked on the inner surface of the vertebral foramen, and a rod for connecting two or more hooks together. Known examples of hook and rod devices are disclosed, for instance, in the PCT patent application n° WO 2005/023126 and in U.S. Pat. No. 4,269,178. However, using hooks may be difficult, especially because their use increases the risk that the physician (or other operative) might contact and potentially damage the spinal cord that extends along the vertebral foramen (which may result in paralysis of the patient).

Another kind of known device is a screw and rod device with screws that are screwed into the vertebrae, and a rod for connecting two or more screws together. A known example of screw and rod device is disclosed, for instance, in European patent n° EP 1575433B1. The screws typically are inserted in pairs into the pedicles of a vertebra, on each side of the spinous process, thereby constituting fixing points on the vertebrae for holding the vertebrae. However, in some cases, the pedicles are small or have deteriorated and may be damaged or do not provide sufficient purchase to permanently hold the screw.

Besides, hook and rod devices, as well as screw and rod devices, generally produce a rigid connection between the rod and each vertebra and, thus, between the vertebrae to be held. However, in some cases it is desirable to allow a controlled relative movement between these vertebrae.

Another kind of known device is disclosed in WO 2009/047352. It comprises a rod, a blocking body surrounding the rod and a ligature. When using such a device, the ligature is passed around a bone and through the blocking body, and the rod is loaded into the blocking body. The ends of the ligature are pulled so as to apply tension to the ligature, the ligature and the rod being simultaneously fastened to the blocking body by means of a fastening system comprising a screw or a nut. Portion(s) of the elongated member are clamped between outer face(s) of the rod and inner face(s) of the blocking body. However, this device does not give complete satisfaction because it may be difficult to handle and/or to operate, especially during the fastening step. Moreover, the manufacturing of this device may be expensive, especially due to the large number of parts that make up the device. Finally, this device takes up much space, especially due to the blocking body which surrounds the rod.

SUMMARY OF THE INVENTION

According to one embodiment of the present disclosure, there is provided a bone holding device comprising:
- at least one conformable elongated member having a first portion, a second portion and an intermediate portion therebetween;
- a rod having at least one passage (which may also be referred to as a hole) which opens into at least one of two opposite side faces of the rod, said passage being delimited by inner surfaces of the rod; and
- at least one compression member being adapted for interacting with said inner surfaces to define clamping surfaces, so that the first and second portions of the elongated member can be inserted and clamped between said clamping surfaces.

The rod extends longitudinally along a main axis and is configured to connect together two bony structures, more particularly two vertebrae, being spaced from each other along the main axis.

The passage is a transverse passage. The transverse passage may extend substantially perpendicularly to the main axis of the rod. The transverse passage may be a through passage which opens into two opposite side faces of the rod.

Compared to the devices of the prior art, such a bone holding device has a simple structure and a quite limited number of parts and is, therefore, easier to handle by the physician (or other operative) and easier to manufacture. Moreover, since the compression member is at least partly located inside the passage of the rod, it does not take up much space outside of the rod and, thus, the volume of the whole device is limited.

The elongated member may be made from a flexible or conformable material that allows a certain amount of movement so that, even after the physician has pulled and locked in position the portions of the elongated member, the elongated member allows a limited amount of relative movement between the bone and the rod while providing a stabilizing effect.

The elongated member may be a band-shaped elongated member such as a ribbon or a strap (i.e. the elongated member may be a thin and wide band of material). Thus, the contact interface between the band-shaped elongated member is also wide, thereby improving the contact and better distributing the stresses on the bony structure, thus avoiding cutting phenomenon.

The elongated member may be made from a polymeric material such as, for example, polyester, polyethylene (for example, polyethylene terephthalate or PET), polyetheretherketone (PEEK) or any other material that provides the desired conformability and flexibility.

According to an embodiment, the transverse passage and the compression member are configured to clamp both the first and second portions of the elongated member in this transverse passage (i.e. the one same transverse passage).

According to an embodiment, the rod comprises at least two transverse passages which are spaced from each other along the main axis.

According to an embodiment, the transverse passage has an elongate cross-section, more particularly an oval (e.g. elliptical) or oblong cross-section, with the longer dimension of the cross section being essentially parallel to the main axis. Such a cross-section is interesting, more particularly, in combination with a band-shaped elongated member.

According to an embodiment, the transverse passage and the compression member are configured so that the first and second portions of the elongated member can be clamped between the compression member and the longer side walls of the passage. More particularly, the longer side walls are parallel to the main axis. Such a configuration is interesting, more particularly, in combination with a band-shaped elongated member.

According to an embodiment, the compression member is deformable, the first and second portions of the elongated member being clamped between the compression member and the rod by deforming said compression member.

According to an embodiment, the compression member is elastically deformable, the elongated member being inserted by force between the compression member and the rod, thereby deforming the compression member into an unstable shape. Once insertion forces are no longer applied, the elongated member being in a desired position, the compression member returns to its original stable shape, thereby clamping the elongated member.

According to another embodiment, the compression member is plastically deformable. In this case, once the elongated member is in a desired position, the compression member is plastically deformed so as to push the elongated member against the rod, thereby clamping the elongated member.

The compression member and the rod may be two distinct pieces or one single piece. In this latter case, the compression member is made out of the same material as the rod, the compression member and the rod having different mechanic behaviors because of their different shapes and thicknesses.

According to an embodiment, the compression member comprises a compression part which is configured to be located, at least partially, inside said passage, and at least one leg extending from said compression part and being configured so that the compression member can be clipped onto the rod.

According to an embodiment, said leg(s) surrounds at least partially the outline of the section of the rod. For instance, the compression member comprises two legs extending from said compression part in opposite directions, each leg surrounding partially the outline of the rod section.

Thus, before implanting the device, the compression member and the rod may be pre-assembled by clipping, thereby reducing the risk of loosing the compression member and making the device safer and easier to use. Once the device is implanted, the engagement by clipping reduces the risk of disengagement of the compression member.

According to an embodiment, the compression member is provided with a thread for rotative engagement with a complementary thread provided on the rod, the first and second portions of the elongated member being clamped between the compression member and the rod by tightening the compression member relative to the rod.

Due to the above-mentioned rotative engagement, the clamping of the elongated member can be easily adjusted as desired. Moreover, the compression member and the rod may be pre-assembled by screwing before implanting the device, thereby reducing the risk of loosing the compression member and making the device safer and easier to use. Once the device is implanted, rotative engagement reduces the risk of disengagement of the compression member.

According to an embodiment, the compression member is provided with protrusions on its clamping surfaces. Said protrusions may be peripheral ribs or fins jutting out of the lateral faces of the compression member, the compression member having, for instance, a fir tree configuration. Such protrusions penetrate into the elongated member, thereby preventing the elongated member from sliding with respect to the clamping surfaces and/or reducing the risk of disengagement of the compression member.

According to an embodiment, the compression member is spring-mounted to the rod by means of a spring which urges the compression member toward the clamping surfaces of the rod, the first and second portions of the elongated member being clamped between the compression member and the rod when the compression member is urged toward said clamping surfaces.

In this embodiment, the physician (or other operative) may need to push in the compression member in order to insert the first and second portions of the elongated member between the compression member and the rod. In this case, by releasing the pressure on the compression member, the elongated member is "automatically" clamped.

According to an embodiment, the inner surfaces delimiting the passage of the rod are deformable, the first and second portions of the elongated member being clamped between the compression member and the rod by deforming said inner surfaces.

According to an embodiment, said inner surfaces are plastically deformable. Thus, once the elongated member is in a desired position, said inner surfaces are plastically deformed, typically from the outside of the rod, so as to push the elongated member against the compression member, thereby clamping the elongated member.

A tool such as pliers may be used for deforming said inner surfaces. Each inner surface may be defined on the inner side of a wall forming part of the rod, this wall having a limited thickness so as to be easily deformed.

According to an embodiment, the first and second portions of the elongated member are provided with a stiff tip. Such stiff tips make the insertion of the first and second portions into the passage and between the clamping surfaces easier.

According to an embodiment, the first and second portions of the elongated member are provided with protrusions. Such protrusions increase the friction between the elongated member and said clamping surface, so that the elongated member is held between these surfaces.

According to an embodiment, the rod comprises at least one portion provided with one passage, said portion(s) having a section which is larger than the average section of the rod. Thus, the loss of mechanical strength due to the presence of the passage is compensated, at least in part, by the section increase.

According to one embodiment of the present disclosure, there is also provided a method for holding a bone in position, comprising the steps of:

providing a bone holding device as above-described;

passing the intermediate portion of a first elongated member around a first bony structure (which may also be referred to as a first bone) and the first and second portions of the first elongated member through a first passage of the rod;

applying tension to the first elongated member by pulling on the ends of the first elongated member;

fastening the first elongated member to the rod by clamping the portions of the first elongated member between a first compression member and the rod.

According to an embodiment, the method further comprises the steps of:

passing the intermediate portion of a second elongated member around a second bony structure (which may also be referred to as a second bone) and the first and second portions of the second elongated member through a second passage of said rod;

applying tension to the second elongated member by pulling on the ends of the second elongated member;

fastening the second elongated member to said rod by clamping the first and second portions of the second elongated member between a second compression member and the rod.

Typically, the physician uses a number of elongated members and compression members corresponding to the number of bony structures to be held, with one rod connecting together the elongated members and, thus, the bony structures.

The above method makes it possible to hold two or more bony structures, in a desired relative position.

Said first and/or second bony structure may be a vertebra, especially a lamina or a transverse process of a vertebra, and the method may be used for holding two or more vertebrae in a desired relative position, so as to treat abnormal curvature of the spine.

Such a method has further advantages linked to the use of a bone holding device according to the disclosure. Especially, this method is easy to implement.

BRIEF DESCRIPTION OF THE DRAWINGS

In the drawings, like reference signs generally refer to the same parts throughout the different views. Moreover, parts of different embodiments having the same or analogous function are identified by the same reference sign.

The drawings are not necessarily to scale, emphasis instead being placed upon illustrating the principles of the invention.

FIG. 1 is a partial view of a first example of rod.

FIG. 2 is a sectional view of a first example of bone holding device, comprising the rod of FIG. 1, this rod being sectioned in plane II-II.

FIG. 3 is a sectional view, like that of FIG. 2, of another example of bone holding device.

FIG. 4 is a partial view of another example of bone holding device.

FIG. 5 is a sectional view of the device of FIG. 4, in plane V-V.

FIG. 6 is a sectional view, like that of FIG. 4, of another example of bone holding device.

DETAILED DESCRIPTION OF THE INVENTION

Figure 7:
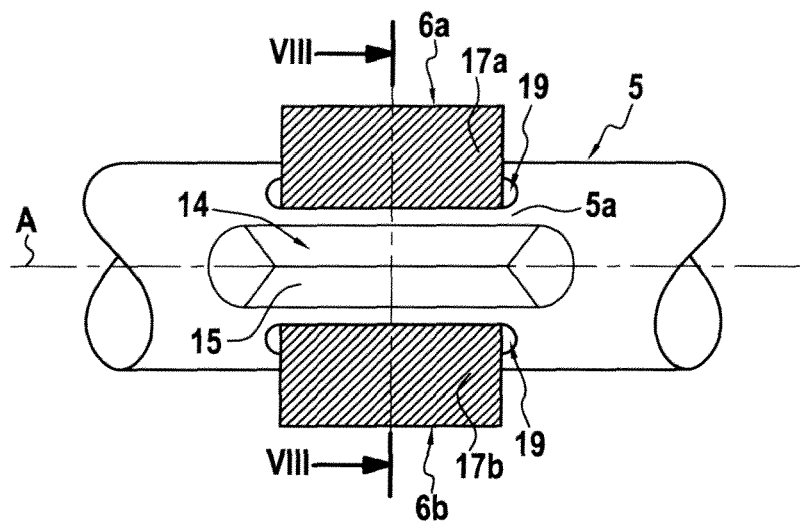
FIG. 7 is a partial view of another example of bone holding device.

FIGS. 1 to 15 show different examples of bone holding devices according to the present disclosure, each of them comprising:

at least one conformable elongated member 7 having a first portion 7a, a second portion 7b and an intermediate portion 7c therebetween;

a rod 5 to which the first and second portions 7a, 7b, are to be secured; and at least one compression member 14.

The rod 5 comprises several passages 8, 8', 8". In other embodiments, the rod 5 can include a single passage. Each passage 8, or hole, is a through hole opening into two opposite side faces 5a, 5b of the rod 5, i.e. each passage 8 goes through the rod 5, from a first side face 5a of the rod to a second side face 5b which is substantially opposed to the first one with respect to the main axis A of the rod 5. In other embodiments, the passage may not pass through the entire rod 5. The side faces 5a, 5b are so called in contrast with the end faces (not shown on the drawings) of the rod 5, both the side and end faces being outer faces of the rod 5.

Each passage 8 is delimited by inner surfaces 9 of the rod 5. These inner surfaces 9 and the compression member 14 both define clamping surfaces 14a, 9a, such that the clamping surfaces 14a of the compression member 14 face the clamping surfaces 9a of the inner surfaces 9, once the compression member 14 is properly positioned within the passage 8.

The compression member 14 and the inner surfaces 9 cooperate so that the portions 7a, 7b, of the elongated member 7 can be inserted and clamped between the clamping surfaces 14a, 9a.

The compression member 14 may be made from polymeric material such as, for example, polyethylene, polyetheretherketone (PEEK), silicon or from metallic material such as, for example, titanium (for example, pure, alloy, beta), stainless steel, cobalt chromium.

The rod 5 may be made from polymeric material such as, for example, polyetheretherketone (PEEK) or from metallic material such as, for example, titanium (for example, pure, alloy, beta), stainless steel, cobalt chromium or any other material providing enough stiffness for holding one or several bones in a desired configuration.

In one embodiment, the elongated member 7 is a tie having a band shape. In other embodiments, the elongate member 7 may be a cord or other shape. It may be made from a polymeric material such as, for example, polyester, polyethylene (for example, PET), polyetheretherketone (PEEK) or any other material that provides the desired conformability and a certain amount of elasticity. For example, it may be made by weaving.

The devices of FIGS. 1 to 15 may be used by a physician, or another operative, as follows:

the intermediate portion 7c of a first elongated member 7 is passed around a first bone (not shown) and the first and second portions 7*a*, 7*b* of the first elongated member 7 are passed through a first passage 8 of the rod 5;

tension is applied to the first elongated member 7 by pulling on its ends 6*a*, 6*b*; and the first elongated member 7 is fastened to the rod 5 by clamping its first and second portions 7*a*, 7*b* between a first compression member 14 and the inner surfaces 9 of the first passage 8.

In one procedure, one of the ends 6*a*, 6*b* of the first elongated member 7 may be passed through a first passage 8 of the rod 5, passed around bony anatomy (not shown), and then passed back through the passage 8 of the rod 5 for subsequent tensioning and clamping. The ends 6*a*, 6*b* may be any portion of the elongated member 7 that extends outside of the passage 8 of the rod 5 opposite the intermediate portion 7*c* of the elongated member 7.

In some cases, for passing the first elongated member 7 through the passage 8 of the rod 5, it may be necessary to use a special tool, such as a needle, having a shape adapted to that of the passage 8.

Also, for applying tension to the first elongated member 7 and/or for fastening the first elongated member 7 to the rod 5, it may be necessary to use a special tool.

When two bones need to be held in a relative position, the method further comprises the following steps:

an intermediate portion of a second elongated member (not shown) is passed around a second bone (not shown) and first and second portions of the second elongated member are passed through a second passage 8' (or 8") of said rod 5;

tension is applied to the second elongated member by pulling on its ends;

the second elongated member is fastened to said rod 5 by clamping the first and second portions between a second compression member (not shown) and the inner surfaces 9' of the second passage 8'.

When more than two bones need to be held in a relative position, the above-mentioned steps are repeated, as many elongated members, compression members and passages as necessary being used.

The number of passages 8, 8', 8", may be higher than the number of bones to be held, which allows one to select a passage depending on the position of the bone to be held. In other embodiments, the rod may have a single passage.

In the examples of FIGS. 1 to 15, the rod 5 extends along a main axis A (see FIGS. 1, 4, 7, 10, 14). In the present disclosure, the axial direction corresponds to the direction of the main axis A of the rod 5, and a radial direction is a direction perpendicular to axis A and intersecting axis A. Similarly, an axial plane is plane containing axis A, and a radial plane is a plane perpendicular to axis A. Unless specified to the contrary, the adjectives and adverbs "axial", "axially", "radial" and "radially" are used relative to the above-mentioned axial and radial directions. Accordingly, the sectional views of FIGS. 2, 3, 5, 6, 8, 9, 11, 12, 13 and 15, are radial sectional views.

In the example of FIGS. 1 and 2, the rod 5 has a radial section which is round and constant along the main axis A of the rod 5, and the compression member 14 is separable from the rod 5. However, the radial section of the rod 5 may have other shapes (for example, an oval), may not be constant along its main axis A, and may include varying degrees of curvature.

Each passage 8, 8', 8" has an opening section, or cross-section, with an oblong shape extending axially, as shown in FIG. 1. Thus, the longer dimension of the cross-section is parallel to the main axis A and the longer side walls of the passage 8 are parallel to the main axis A.

The compression member 14 is a wedge configured to be inserted into the passage 8. The axial length (i.e. the length in the direction of the main axis A) of the compression member 14 is smaller than the axial length of the passage 8 and, preferably, larger than the width of the elongated member 7.

As shown in FIG. 2, in radial section, the compression member 14 has a tapered tip portion 14*b*. Once the elongated member 7 is in a desired position, this tip portion 14*b* of the compression member 14 is inserted by force into the passage 8, and the elongated member 7 is clamped between clamping surfaces 14*a*, defined by the side faces of the tip portion 14*b*, and the clamping surfaces 9*a* defined by the inner surfaces 9 surrounding the passage 8.

As shown in FIG. 2, the clamping surfaces 14*a* of the compression member 14 have a concave profile whereas the clamping surfaces 9*a* of the of the rod 5 have a convex profile. The cooperation between the concave and convex profiles reduces the risk of disengagement of the compression member 14.

Another example of bone holding device is shown in FIG. 3. This example differs from the one of FIG. 2 in that the clamping surfaces 14*a* of the compression member 14 have protrusions 30 (instead of a concave profile) and in that the inner surfaces 9 of the passage 8 have a straight profile (instead of a convex profile). Due to the protrusions 30, the radial section of the tapered tip portion 14*b* of the compression member 14 has a fir tree shape. The protrusions 30 prevent relative movement between the compression member 14 and the elongated member 7.

In the example of FIGS. 4 and 5, the rod 5 has a varying radial section along its main axis. The rod 5 has portions 5' with a larger section and portions 5" with a smaller section. Portions 5' and 5" are alternated in the axial direction. Each portion 5' is provided with one passage 8 (8', 8"). Thus, the loss of mechanical strength due to the presence of a passage 8 is compensated, at least in part, by the section increase, the weight of the rod 5 remaining limited.

As shown in FIG. 5, the compression member 14 has a central compression part 14*c* having a V-shaped profile and being configured to be partially inserted into the passage 8, and two legs 14*d* extending from said compression part 14*c* and encircling partially the outline of the radial section of the rod 5, so that the compression member 14 can be clipped onto the rod 5. As shown in FIG. 5, in radial section, the proximal end of each leg 14 is connected to the central compression part 14*c* in the vicinity of one opening of the passage 8, then each leg 14 follows the outline of the rod 5, and the distal end of each leg 14 is located in the vicinity of the other opening of the passage 8.

The first and second portions 7*a*, 7*b* of the elongated member 7 are clamped between the clamping surfaces 14*a* of the compression part 14*c* and is the inner surfaces 9 of the rod 5.

Another example of bone holding device is shown in FIG. 6. This example differs from that of FIG. 5 in that the clamping surfaces 14*a* of the compression part 14*c* have protrusions 30.

Figure 8:
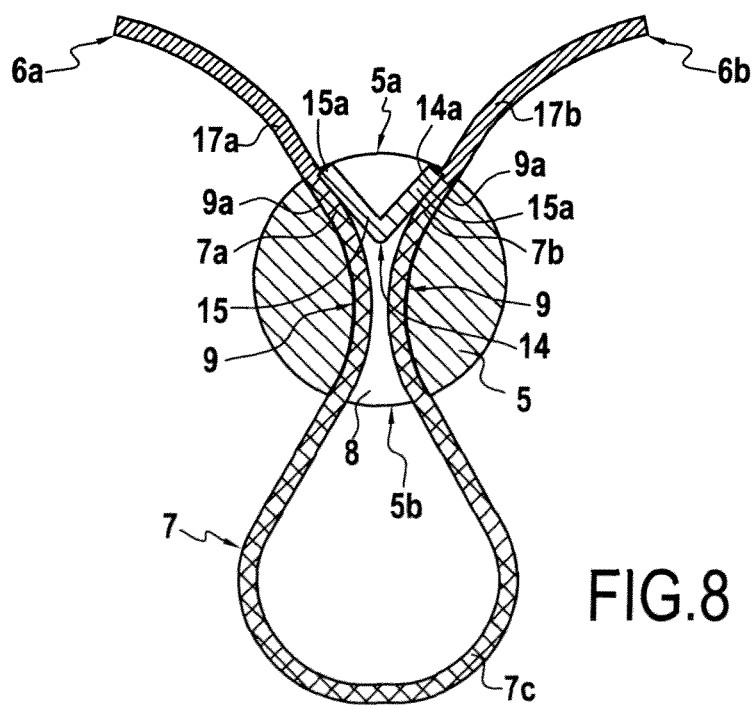
FIG. 8 is a sectional view of the device of FIG. 7, in plane VIII-VIII.

In the example of FIGS. 7 and 8, the compression member 14 and the rod 5 form one single piece. The compression member 14 is a pushed-in external wall 15 of the rod 5 and the passage 8 opens into the side face 5*a* of the rod 5, on each side of the compression member 14, thereby forming two passages 19 (see FIG. 7) surrounding the compression member 14. Each passage 19 is defined between the compression member 14 and an inner surface 9 of the rod 5.

The compression member 14 in radial section has a "V" shape. The compression member 14 is elastically deformable between an original stable configuration, wherein the arms 15a of the V-shaped compression member 14 are spaced-apart, and an unstable configuration wherein the arms 15a of the "V" shaped compression member 14 are close together. When the compression member 14 is in its original stable configuration, the width of each passage 19 is smaller than the thickness of the elongated member 7.

The elongated member 7 is inserted by force through the passages 19. In order to make the insertion easier, the portions 7a, 7b of the elongated member 7 may have, respectively, stiff tips 17a, 17b. Once insertion forces are no longer applied, the elongated member 7 being in a desired position, the compression member 14 returns to its original stable shape, i.e. arms 15a move apart, thereby clamping the elongated member 7 between the arms 15a and the rod 5.

Figure 9:
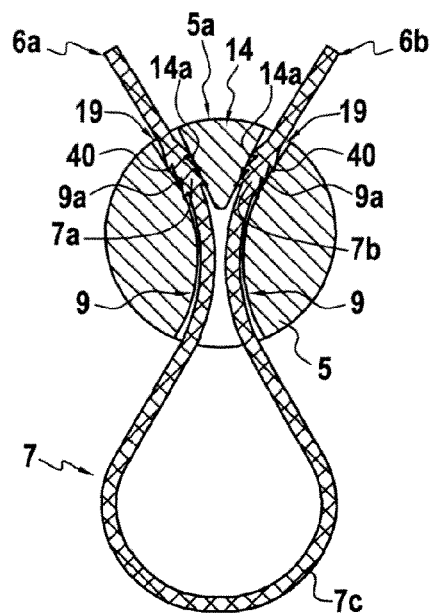
FIG. 9 is a sectional view, like that of FIG. 8, of another example of bone holding device.

In the example of FIG. 9, the compression member 14 and the rod 5 form one single piece. The passage 8 opens into the side face 5a of the rod 5, on each side of the compression member 14, thereby forming two passages 19 surrounding the compression member 14. Each passage 19 is defined between the compression member 14 and an inner surface 9 of the rod 5.

The first and second portions 7a, 7b of the elongated member 7 have protrusions 40 forming folds or ribs on their outer surface. These protrusions 40 are distant from the extremities of the elongated member 7.

Each portion 7a, 7b of the elongated member 7 is inserted by force through a passage 19. When the protrusions 40 enter into the passage 19, the friction between the elongated member 7 and the clamping surfaces 14a, 9a increases until locking of the protrusions 40 in the passage 19 occurs, so these protrusions 40 are clamped between the compression member 14 and the rod 5.

For instance, the protrusions 40 are made from polymeric material such as polyethylene, polyetheretherketone (PEEK), silicon or from metallic material such as, for example, titanium (for example, pure, alloy, beta), stainless steel, cobalt chromium. These protrusions 40 may be added-on pieces encased in the elongated member 7 during its manufacturing process, e.g. during the weaving of the elongated member 7.

Figure 10:
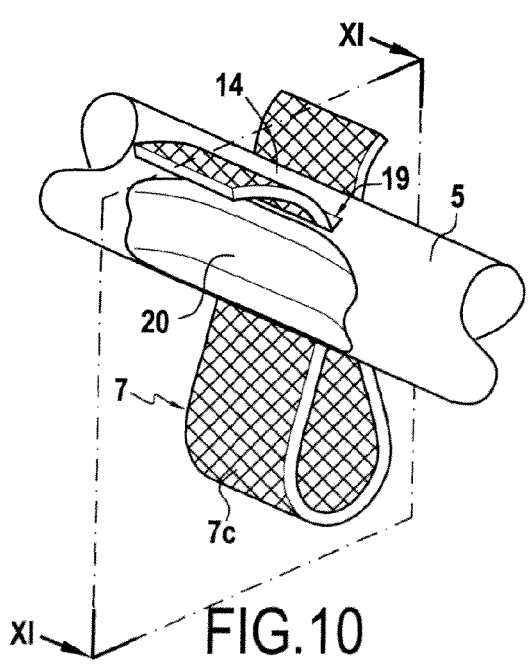
FIG. 10 is a partial perspective view of another example of bone holding device.
Figure 11:
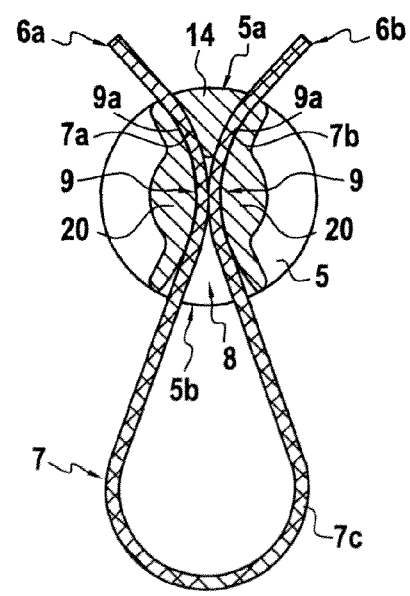
FIG. 11 is a sectional view of the device of FIG. 10, in plane XI-XI.

Another example of bone holding device is shown in FIGS. 10 and 11. In this example, the compression member 14 and the rod 5 form one single piece. The passage 8 opens into the side face 5a of the rod 5, on each side of the compression member 14, thereby forming two passages 19 (see FIG. 10) surrounding the compression member 14. Each passage 19 is defined between the compression member 14 and an inner surface 9 of the rod 5.

Each inner surface 9, which delimits the passage 8, is defined on the inner side of an external wall 20 forming part of the rod 5 and having a limited thickness so as to be easily deformed. Once the elongated member 7 is in a desired position, the wall 20 is plastically deformed, from the outside of the rod 5, so as to push and clamp the elongated member 7 against the compression member 14.

A tool such as pliers (not shown) may be used for deforming the walls 20. In order to make the deformation of the walls 20 easier, these walls 20 may have memory shape properties.

Figure 12:
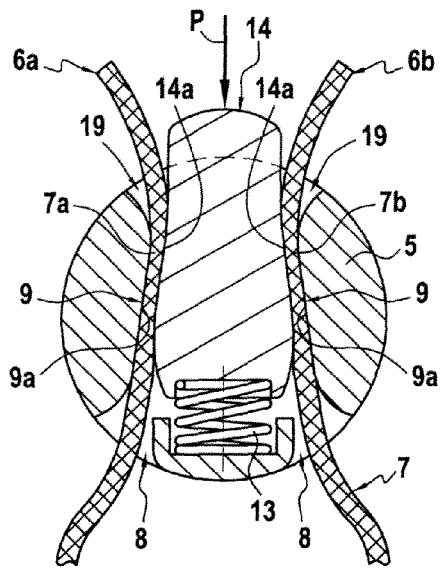
FIG. 12 is a sectional view of another example of bone holding device.
Figure 13:
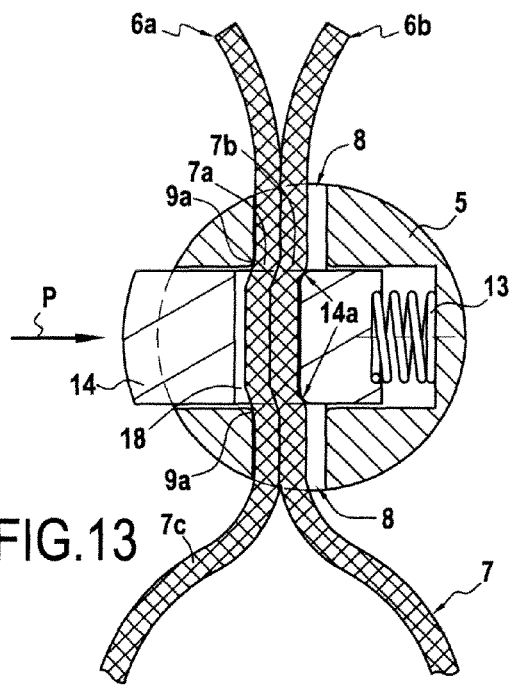
FIG. 13 is a sectional view of another example of bone holding device.

Two other examples of bone holding devices are shown in FIGS. 12 and 13. In both examples, the compression member 14 is spring-mounted to the rod 5 by means of a spring 13 which urges the compression member 14 toward the clamping surfaces 9a of the rod 5, the first and second portions 7a, 7b of the elongated member being clamped between the compression member 14 and the rod 5 when the compression member is urged toward said clamping surfaces 9a. In both examples, the physician (or other operative) need to push in the compression member 14 (see arrow P) in order to pass the first and second portions 7a, 7b through the passage 8. By releasing the pressure on the compression member 14, the elongated member 7 is "automatically" clamped between the compression member 14 and the rod 5.

In the example of FIG. 12, the compression member 14 extends in the same direction as the passage 8. Thus, there exist two secondary passages 19, on each side of the compression member 14, each secondary passage 19 being defined between the compression member 14 and an inner surface 9 of the rod. The portions 7a, 7b of the elongated member 7 are passed through these secondary passages 19.

In the example of FIG. 13, the compression member 14 extends in the a direction substantially perpendicular to that of the passage 8 (called first passage 8) of the rod 5. The compression member 14 comprises a second passage 18 extending in the same direction as that of the first passage 8. When the compression member 14 is pushed in the first and second passages 8, 18, are aligned and the first and second portions 7a, 7b of the elongated member 7 can be passed through these passages 8, 18. When the compression member 14 is released, the first and second passages 8, 18 become misaligned and the elongated member 7 is clamped between the clamping surfaces 14a and 9a.

Figure 14:
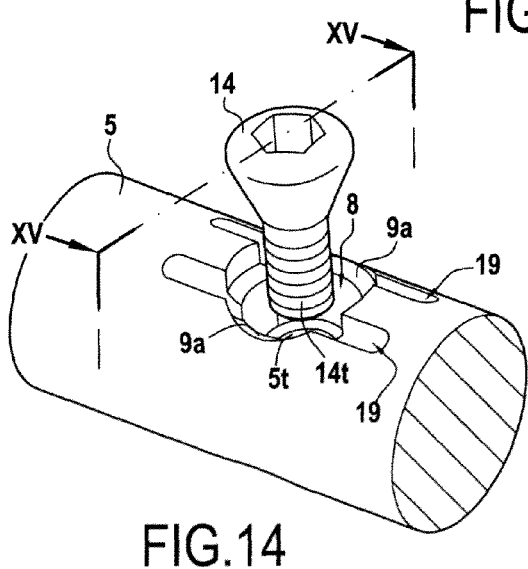
FIG. 14 is a partial perspective view of another example of bone holding device.
Figure 15:
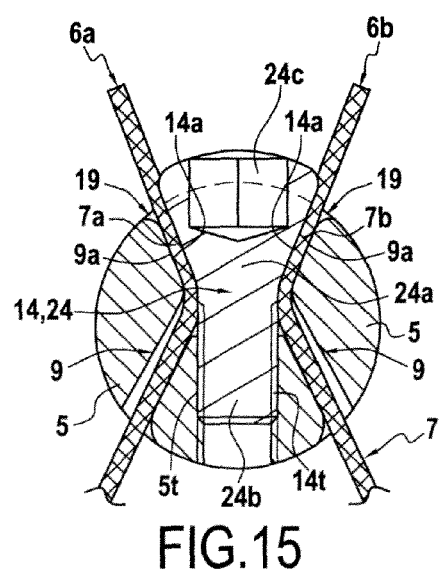
FIG. 15 is a sectional view of the device of FIG. 14, in plane XV-XV.

Another example of bone holding device is shown in FIGS. 14 and 15. In this example, the compression member 14 is provided with a thread 14t for rotative engagement with a complementary thread 5t provided on the rod, the first and second portions 7a, 7b of the elongated member 7 being clamped between the compression member 14 and the rod 5 by tightening (by rotating) the compression member 14 relative to the rod 5.

More particularly, the compression member 14 is a screw 24 with a head 24a and a shaft 24b. The screw head 24a has a profile 24c (or screw drive) that allows the screw to be driven. The screw shaft 24b is provided with the external thread 14t. The screw shaft 24b can engage with a complementary thread 5t of a threaded hole provided in the rod 5. The screw 24 extends in substantially the same direction as the passage 8. The screw head 24a has a tapered shape, a truncated shape in the example. One opening of the passage 8 is funnel-shaped, so that it can receive the screw head 24a. When the screw 24 is rotatably tightened, the screw head 24a bears on the surfaces of the funnel-shaped opening.

There exist two passages 19, on each side of the compression member 14, each passage 19 being defined between the compression member 14 and an inner surface 9 of the rod. The first and second portions 7a, 7b of the elongated member 7 can be passed through these passages 19 and clamped between the clamping surfaces 14a of the screw head 24a and the clamping surfaces 9a of the rod 5, as shown on FIG. 15.

The above description is given by way of example, and not limitation. Given the above disclosure, one skilled in the art could devise variations that are within the scope of the invention disclosed herein. Further, the various features of the embodiments or examples disclosed herein can be used alone or in varying combinations with each other, and are not intended to be limited to the specific combination described herein.

The invention claimed is:
1. A bone holding device comprising:
at least one elongated member having a first portion, a second portion and an intermediate portion therebetween, a cylindrical rod extending longitudinally along a main axis and a length sufficient to extend between a first vertebra and a second vertebra, the rod being adapted to connect together the first and second vertebrae spaced from each other along the main axis, the rod having at least one transverse passage extending transverse to the main axis which opens into at least one of two opposite side faces of the rod, said passage being delimited by inner surfaces of the rod, the rod having a circular cross-section transverse to the main axis, and at least one compression member being adapted for insertion into the at least one transverse passage in a direction transverse to the main axis and interacting with said inner surfaces to define clamping surfaces, so that the first and second portions of the elongated member can be inserted and clamped between said clamping surfaces.

2. A bone holding device according to claim 1, wherein the compression member and the rod are two distinct pieces, the compression member being moveable relative to the rod, the first and second portions of the elongated member being clamped between the compression member and the rod by moving the compression member relative to the rod.

3. A bone holding device according to claim 1, wherein said passage and the compression member are configured to clamp both the first and second portions of the elongated member in said passage.

4. A bone holding device according to claim 1, wherein the rod comprises at least two transverse passages which are spaced from each other along the main axis.

5. A bone holding device according to claim 1, wherein said passage has an elongate cross-section having a longer dimension and a shorter dimension transverse to the longer dimension with the longer dimension of the cross-section being essentially parallel to the main axis.

6. A bone holding device according to claim 1, wherein the compression member includes clamping surfaces facing the clamping surfaces of the rod.

7. A bone holding device according to claim 6, wherein the clamping surfaces of the compression member have a concave profile.

8. A bone holding device according to claim 7, wherein the clamping surfaces of the rod have a convex profile.

9. A bone holding device according to claim 1, wherein the compression member includes a tapered tip portion.

10. A bone holding device comprising:
an elongated member having a first portion, a second portion and an intermediate portion therebetween,
a cylindrical rod extending longitudinally along a longitudinal axis of the rod, the rod being adapted to connect together two vertebrae spaced from each other along the longitudinal axis, the rod having a first transverse passage extending perpendicular to the longitudinal axis which opens into at least one of two opposite side faces of the rod, the transverse passage being delimited by inner surfaces of the rod, the rod having a circular cross-section transverse to the longitudinal axis, and
a compression member being adapted for insertion into the at least one transverse passage in a direction perpendicular to the main axis and interacting with said inner surfaces to define clamping surfaces, so that the first and second portions of the elongated member can be inserted and clamped between said clamping surfaces.

11. The bone holding device of claim 10, wherein the rod includes a second transverse passage longitudinally spaced apart from the first transverse passage along the longitudinal axis of the rod.

12. The bone holding device of claim 10, wherein the clamping surfaces of the rod have a convex profile and the compression member includes clamping surfaces having a concave profile facing the clamping surfaces of the rod.

13. A bone holding device comprising:
an elongated member having a first portion, a second portion and an intermediate portion therebetween,
a cylindrical rod extending longitudinally along a longitudinal axis of the rod, the rod being adapted to connect together two vertebrae spaced from each other along the longitudinal axis, the rod having a transverse passage extending transverse to the longitudinal axis which opens into at least one of two opposite side faces of the rod, the transverse passage being delimited by inner surfaces of the rod, the rod having a circular cross-section transverse to the longitudinal axis, and
a compression member being adapted to be inserted into the transverse passage in a direction transverse to the longitudinal axis of the rod, the compression member adapted for interacting with said inner surfaces to define clamping surfaces, so that the first and second portions of the elongated member can be inserted and clamped between said clamping surfaces.

14. The bone holding device of claim 13, wherein the compression member is insertable into the transverse passage without rotation of the compression member.

* * * * *